(12) United States Patent
Takahashi (10) Patent No.: US 10,481,131 B2
(45) Date of Patent: Nov. 19, 2019

(54) ULTRASONIC TEST SYSTEM, ULTRASONIC TEST METHOD AND METHOD OF MANUFACTURING AIRCRAFT PART

(71) Applicant: FUJI JUKOGYO KABUSHIKI KAISHA, Tokyo (JP)

(72) Inventor: Kohei Takahashi, Tokyo (JP)

(73) Assignee: SUBARU CORPORATION, Tokyo (JP)

( * ) Notice: Subject to any disclaimer, the term of this patent is extended or adjusted under 35 U.S.C. 154(b) by 398 days.

(21) Appl. No.: 15/062,543

(22) Filed: Mar. 7, 2016

(65) Prior Publication Data

US 2016/0274062 A1 Sep. 22, 2016

(30) Foreign Application Priority Data

Mar. 18, 2015 (JP) .................................. 2015-054345

(51) Int. Cl.
*G01N 29/04* (2006.01)
*G01N 29/34* (2006.01)
(Continued)

(52) U.S. Cl.
CPC .............. *G01N 29/041* (2013.01); *B23P 6/00* (2013.01); *G01N 29/043* (2013.01); *G01N 29/12* (2013.01);
(Continued)

(58) Field of Classification Search
CPC .... G01N 29/041; G01N 29/043; G01N 29/12; G01N 29/348; G01N 2291/0289; B23P 6/00

See application file for complete search history.

(56) References Cited

U.S. PATENT DOCUMENTS 4,699,007 A 10/1987 Kawashima et al.
4,744,250 A 5/1988 Ganglbauer et al.
(Continued)

FOREIGN PATENT DOCUMENTS

CN 86106835 A 7/1987
CN 1865981 A 11/2006
(Continued)

OTHER PUBLICATIONS

Vandeputte, et al., Influence of planar cracks in plates on reflected and transmitted fields of Gaussian acoustic beams. *The Journal of the Acoustical Society of America, American Institute of Phsycis for the Acoustical Society of America*, New York, US, vol. 114. No. 2, Aug. 1, 2003, pp. 634-643.
(Continued)

*Primary Examiner* — Tarun Sinha
(74) *Attorney, Agent, or Firm* — Smith, Gambrell & Russell, LLP (57) ABSTRACT

According to one implementation, an ultrasonic test system includes an ultrasonic transmission part including at least one ultrasonic transducer, an ultrasonic detection part including at least one sensor and damage detection part consisting of circuitry. The ultrasonic transducer transmits a first ultrasonic wave and a second ultrasonic wave toward a test region. The first ultrasonic wave has a relatively low frequency. The second ultrasonic wave has a frequency higher than the frequency of the first ultrasonic wave. The sensor detects a reflected wave of the first ultrasonic wave and the second ultrasonic wave which has passed through the test region. The reflected wave is from the test region. The damage detection circuitry is configured to detect a damage in the test region, based on the reflected wave of the first ultrasonic wave and the second ultrasonic wave which has passed through the test region.

22 Claims, 8 Drawing Sheets

(51) Int. Cl.
    *B23P 6/00* (2006.01)
    *G01N 29/12* (2006.01)
(52) U.S. Cl.
    CPC ... *G01N 29/348* (2013.01); *G01N 2291/0289* (2013.01); *G01N 2291/044* (2013.01); *G01N 2291/048* (2013.01); *G01N 2291/0427* (2013.01); *G01N 2291/2694* (2013.01)

(56) References Cited

U.S. PATENT DOCUMENTS

| | | | | |
|---|---|---|---|---|
| 5,303,590 | A * | 4/1994 | Modderman | G01N 29/07 73/588 |
| 6,032,534 | A | 3/2000 | Sherwin | |
| 8,043,220 | B2 * | 10/2011 | Okada | A61B 8/00 600/459 |
| 9,683,880 | B2 * | 6/2017 | Takemura | G01F 1/66 |
| 2005/0067559 | A1 | 3/2005 | Ogisu et al. | |
| 2006/0201252 | A1 | 9/2006 | Georgeson et al. | |
| 2010/0011865 | A1 * | 1/2010 | Saxena | G01N 29/11 73/632 |

FOREIGN PATENT DOCUMENTS

| | | |
|---|---|---|
| CN | 101666783 A | 3/2010 |
| CN | 101966088 A | 2/2011 |
| CN | 102288683 A | 12/2011 |
| JP | S61-025057 | 2/1986 |
| JP | H11-211700 | 8/1999 |
| JP | 2003-185642 | 7/2003 |
| JP | 2004-347549 | 12/2004 |
| JP | 2011-185921 | 9/2011 |
| JP | 2014-194379 | 10/2014 |

OTHER PUBLICATIONS

Extended European Search Report dated Jul. 29, 2016 in European Patent Application No. 16 158 078.2 (9 pages).
Soejima, Hideki et al., Development of Structural Health Monitoring Technology Using Lamb Waves, Subaru Technical Review, Japan, Jun. 2011, No. 38, pp. 150-156 and cover. (English Abstract on p. 3).
First Japanese office action dated Aug. 30, 2016, in Japanese Patent Application No. 2015-054345 (3 pages).
English translation of Japanese Office Action dated Aug. 30, 2016, in Japanese Patent Application No. 2015-054345 (3 pages).
Final Office Action dated Feb. 28, 2017, in Japanese Patent Application No. 2015-054345 (6 pages in Japanese with English machine translation).
Office Action dated May 13, 2019 for European Patent Application No. 16 158 078.2 (4 pages).
Office Action dated Aug. 2, 2019 for Chinese Patent Application No. 201610153821.8 (10 pages in Chinese with Machine Translation).
Search Report dated Jul. 26, 2019 for Chinese Patent Application No. 201610153821.8 (2 pages).

* cited by examiner

ULTRASONIC TEST SYSTEM, ULTRASONIC TEST METHOD AND METHOD OF MANUFACTURING AIRCRAFT PART

CROSS REFERENCES TO RELATED APPLICATIONS

This application is based upon and claims the benefit of priority from Japanese Patent Application No. 2015-054345, filed on Mar. 18, 2015; the entire contents of which are incorporated herein by reference.

FIELD

Implementations described herein relate generally to an ultrasonic test system, an ultrasonic test method and a method of manufacturing an aircraft part.

BACKGROUND

Conventionally, an ultrasonic flaw inspection method is known as a method of nondestructively inspecting a structural member of an aircraft or the like. As a specific example, a damage length measurement system which can measure a length of damage, such as delamination or peeling, in an adhesive part or a bonded part, using an actuator which emits ultrasonic waves toward a region to be inspected and an FBG (fiber Bragg grating) sensor for receiving ultrasonic reflected waves reflected in the region to be inspected has been proposed (for example, refer to Japanese Patent Application Publication JP 2011-185921 A and Japanese Patent Application Publication JP 2014-194379 A).

In ultrasonic testing, it is important to enable to detect damage in a range to be tested more certainly.

Thus, an object of the present invention is to enable to nondestructively detect damage of a test target more certainly.

SUMMARY OF THE INVENTION

In general, according to one implementation, an ultrasonic test system includes an ultrasonic transmission part including at least one ultrasonic transducer, an ultrasonic detection part including at least one sensor and damage detection part consisting of circuitry. At least one ultrasonic transducer transmits a first ultrasonic wave and a second ultrasonic wave toward a test region. The first ultrasonic wave has a relatively low frequency. The second ultrasonic wave has a frequency higher than the frequency of the first ultrasonic wave. At least one sensor detects a reflected wave of the first ultrasonic wave and the second ultrasonic wave which has passed through the test region. The reflected wave is from the test region. The damage detection circuitry is configured to detect a damage in the test region, based on the reflected wave of the first ultrasonic wave and the second ultrasonic wave which has passed through the test region.

Further, according to one implementation, an ultrasonic test method includes: transmitting a first ultrasonic wave having a relatively low frequency and a second ultrasonic wave having a frequency higher than the frequency of the first ultrasonic wave toward a test region; detecting a reflected wave, from the test region, of the first ultrasonic wave and the second ultrasonic wave which has passed through the test region; and detecting a damage in the test region, based on the reflected wave of the first ultrasonic wave and the second ultrasonic wave which has passed through the test region.

Further, according to one implementation, a method of manufacturing an aircraft part includes: bonding a patch to a region including a part to be repaired of an aircraft part; transmitting a first ultrasonic wave having a relatively low frequency and a second ultrasonic wave having a frequency higher than the frequency of the first ultrasonic wave toward a test region; obtaining a reflected wave of the first ultrasonic wave and the second ultrasonic wave which has passed through the test region; and manufacturing a repaired aircraft part by repairing the part to be repaired of the aircraft part. The test region is a boundary surface between the region including the part to be repaired and the patch. The reflected wave is from the test region. The reflected wave and the second ultrasonic wave serve as information for monitoring whether a damage has occurred in the test region.

DETAILED DESCRIPTION

An ultrasonic test system, an ultrasonic test method and a method of manufacturing an aircraft part according to implementations of the present invention will be described with reference to the accompanying drawings.

(Configuration and Function)

Figure 1:
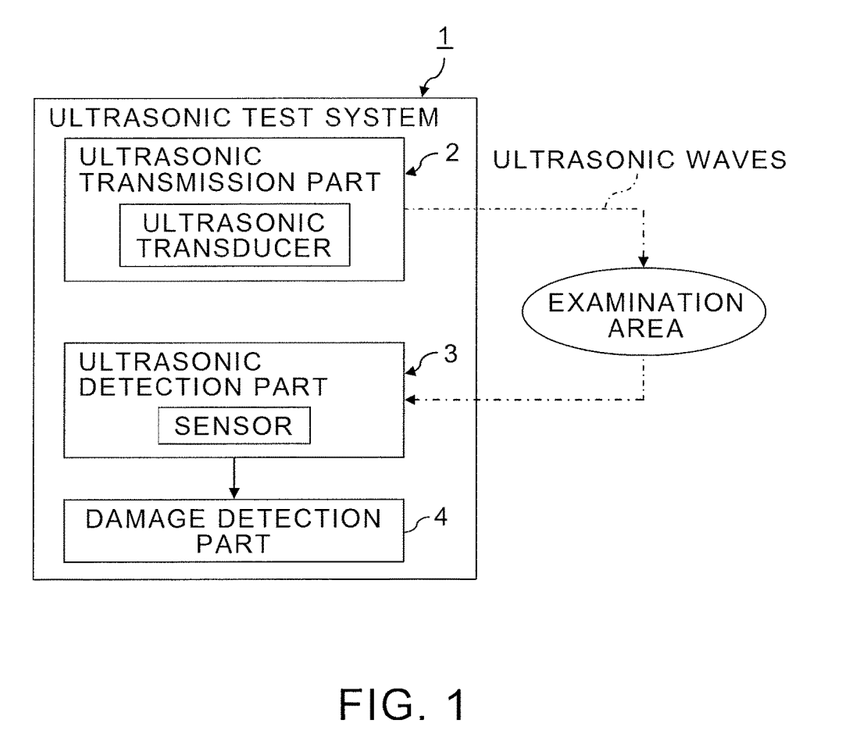
FIG. 1 is a block diagram showing an ultrasonic test system according to an implementation of the present invention.

FIG. 1 is a block diagram showing an ultrasonic test system according to an implementation of the present invention.

An ultrasonic test system 1 performs flaw detection of a test target nondestructively using ultrasonic waves. For that purpose, the ultrasonic test system 1 has an ultrasonic transmission part 2, an ultrasonic detection part 3, and a damage detection part 4. The ultrasonic transmission part 2 transmits ultrasonic waves to a test region, shown as an examination area in FIG. 1, of a test target. The ultrasonic detection part 3 detects the ultrasonic waves transmitted from the ultrasonic transmission part 2. The damage detection part 4 detects damage, such as peeling, delamination, or a crack, in the test region of the test target based on the ultrasonic waves detected in the ultrasonic detection part 3.

Here, characteristic of an ultrasonic wave depending on a frequency will be described. As a result of studying characteristics of an ultrasonic wave depending on a frequency, the following characteristics became clear. The following characteristics can be considered to be common whether a material is metal or a composite material.

When an ultrasonic wave, having a relatively low frequency, whose frequency band is not less than 50 kHz and not more than 150 kHz is transmitted to a test target in which damage exists, an amplitude of a reflected wave caused by reflection at a damaged portion is large while a waveform of an ultrasonic wave which has passed through the damaged portion does not change to an extent sufficient to detect the damage. In particular, when an ultrasonic wave whose frequency band is not less than 75 kHz and not more than 125 kHz is transmitted to a test target in which damage exists, an ultrasonic reflected wave having a satisfactory SNR (signal-to-noise ratio) reflects at a damaged portion. Therefore, when an ultrasonic wave whose frequency band is not less than 75 kHz and not more than 125 kHz is transmitted to a test target in which damage exists, an ultrasonic reflected wave can be detected with practical accuracy.

Meanwhile, when an ultrasonic wave, having a relatively high frequency, whose frequency band is not less than 200 kHz and not more than 500 kHz is transmitted to a test target in which damage exists, an amplitude of a reflected wave caused by reflection at a damaged portion is so small that the reflected wave is difficult to be observed while a waveform of an ultrasonic wave which has passed through the damaged portion changes to an extent sufficient to be observed. Furthermore, an ultrasonic wave having a high frequency can be observed even in a further distance, compared to an ultrasonic wave having a low frequency. In particular, when an ultrasonic wave whose frequency band is not less than 300 kHz and not more than 400 kHz is transmitted to a test target in which damage exists, a waveform change of an ultrasonic wave which has passed through a damaged portion can be detected with practical accuracy.

Based on the above-mentioned study results, the ultrasonic transmission part 2 is composed of at least one ultrasonic transducer which transmits the first ultrasonic wave having a relatively low frequency and the second ultrasonic wave having a relatively high frequency to that of the first ultrasonic wave toward a test region of a test target, respectively. Specifically, the first ultrasonic wave having a low frequency not less than 50 kHz and not more than 150 kHz, desirably not less than 75 kHz and not more than 125 kHz, and the second ultrasonic wave having a high frequency not less than 200 kHz and not more than 500 kHz, desirably not less than 300 kHz and not more than 400 kHz, are transmitted from the ultrasonic transmission part 2 toward a test region of a test target.

On the other hand, the ultrasonic detection part 3 is composed of at least one sensor which detects a reflected wave of the first ultrasonic wave, having a low frequency, in a test region and the second ultrasonic wave, having a high frequency, which has passed through the test region, respectively.

An ultrasonic transducer, such as a piezoelectric element, is used in order to transmit an ultrasonic wave. Meanwhile, a sensor, such as an ultrasonic transducer or an optical fiber sensor, can be used as a sensor for detecting an ultrasonic wave. When an ultrasonic transducer is used as a sensor, an ultrasonic signal is converted into an electric signal in the ultrasonic transducer.

Meanwhile, when an optical fiber sensor is used as a sensor, an ultrasonic signal is converted into an optical signal in the optical fiber sensor. Specifically, when a minute strain occurs in an optical fiber sensor due to vibration by an ultrasonic wave, optical characteristics of the optical fiber sensor change depending on an amount of the strain. As a result, an optical signal having an amplitude depending on an amplitude of the ultrasonic signal can be output from the optical fiber sensor. Examples of an optical fiber sensor include an FBG sensor or a PS-FBG (phase-shifted FBG) sensor. A PS-FBG is an FBG in which a local phase shift has been introduced in periodic change of a refractive index.

Figure 2:
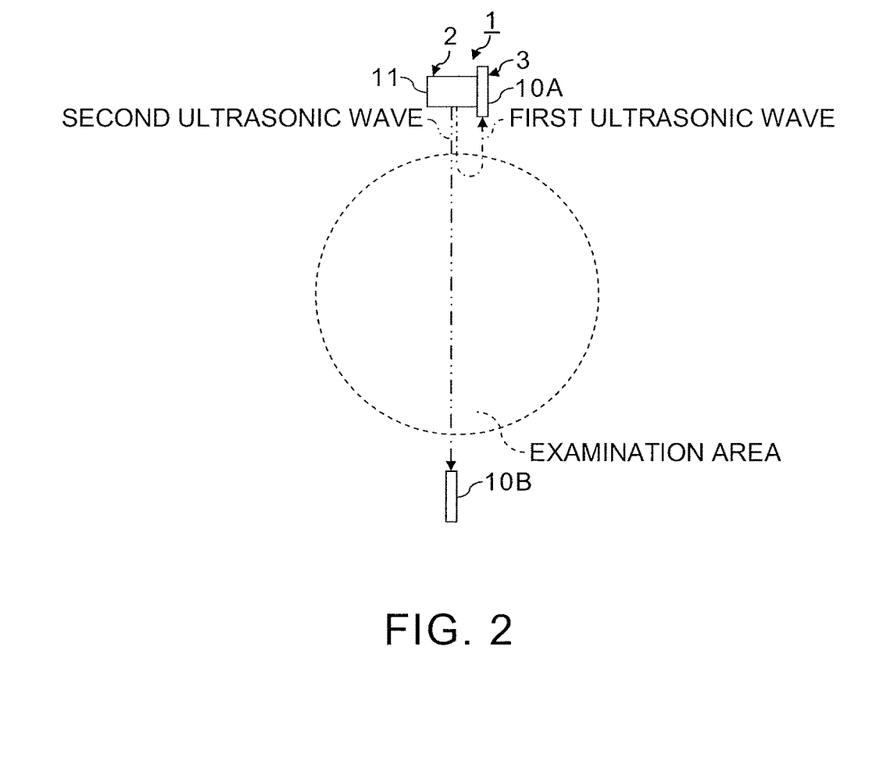
FIG. 2 shows the first example of fundamental structure of the ultrasonic transmission part and the ultrasonic detection part shown in FIG. 1.

FIG. 2 shows the first example of fundamental structure of the ultrasonic transmission part 2 and the ultrasonic detection part 3 shown in FIG. 1.

When an optical fiber sensor 10 is used as a sensor of ultrasonic waves, the ultrasonic transmission part 2 and the ultrasonic detection part 3 can be composed using at least one ultrasonic transducer 11 and at least two optical fiber sensors 10A, 10B as shown in FIG. 2.

Specifically, the ultrasonic transmission part 2 can be composed using one common ultrasonic transducer 11 which sequentially transmits the first ultrasonic wave having a low frequency and the second ultrasonic wave having a high frequency to a test region of a test target. Meanwhile, the ultrasonic detection part 3 can be composed using the first optical fiber sensor 10A and the second optical fiber sensor 10B. The first optical fiber sensor 10A detects a reflected wave of the first ultrasonic wave, having a low frequency, reflected in the test region of the test target. The second optical fiber sensor 10B detects the second ultrasonic wave which has passed through the test region of the test target.

The first optical fiber sensor 10A is disposed in the vicinity of the ultrasonic transducer 11 or the like so as to be able to detect a reflected wave of the first ultrasonic wave. Meanwhile, the second optical fiber sensor 10B is disposed at a position at which the second ultrasonic wave having passed through the test region of the test target can be detected. For example, the second optical fiber sensor 10B can be disposed at a position opposing the ultrasonic transducer 11 so that the test region of the test target lies between the second optical fiber sensor 10B and the ultrasonic transducer 11.

Figure 3:
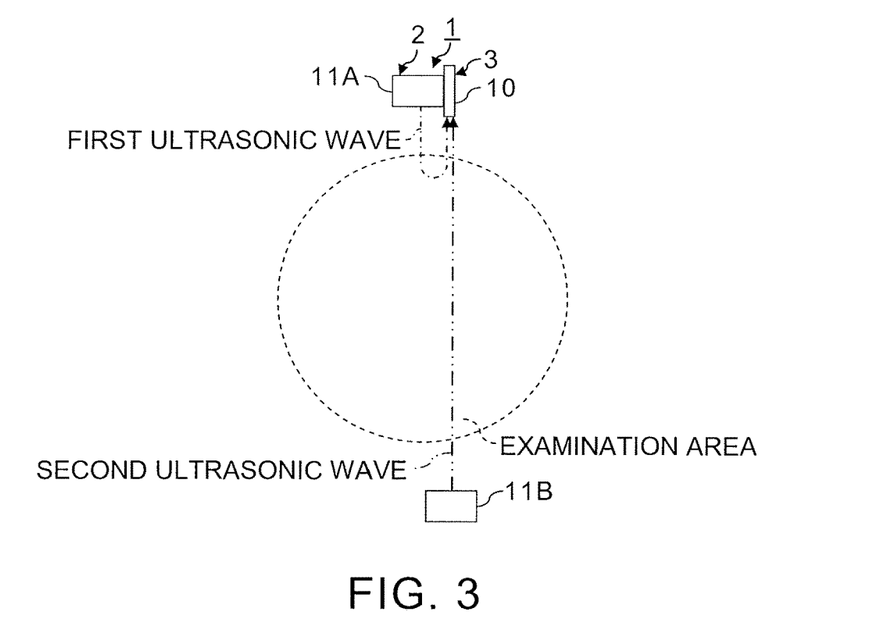
FIG. 3 shows the second example of fundamental structure of the ultrasonic transmission part and the ultrasonic detection part shown in FIG. 1.

FIG. 3 shows the second example of fundamental structure of the ultrasonic transmission part 2 and the ultrasonic detection part 3 shown in FIG. 1.

When the optical fiber sensor 10 is used as a sensor of ultrasonic waves, the ultrasonic transmission part 2 and the ultrasonic detection part 3 can also be composed using at least two ultrasonic transducers 11A, 11B and at least one optical fiber sensor 10 as shown in FIG. 3.

Specifically, the ultrasonic transmission part 2 can be composed using the first ultrasonic transducer 11A and the second ultrasonic transducer 11B. The first ultrasonic transducer 11A transmits the first ultrasonic wave having a low frequency toward a test region of a test target. The second ultrasonic transducer 11B transmits the second ultrasonic wave toward the test region from a direction different from that of the first ultrasonic wave. Meanwhile, the ultrasonic detection part 3 can be composed using one common optical fiber sensor 10 which detects both of a reflected wave of the first ultrasonic wave having a low frequency and the second ultrasonic wave having passed through the test region of the test target.

In this case, the first ultrasonic transducer 11A is disposed in the vicinity of the optical fiber sensor 10 or the like so that the reflected wave of the first ultrasonic wave from the test region can be detected in the optical fiber sensor 10. Meanwhile, the second ultrasonic transducer 11B is positioned so that the second ultrasonic wave which has passed through the test region of the test target can be detected in the optical fiber sensor 10. For example, the second ultrasonic transducer 11B can be disposed at a position opposing the optical fiber sensor 10 so that the test region of the test target lies between the second ultrasonic transducer 11B and the optical fiber sensor 10.

Figure 4:
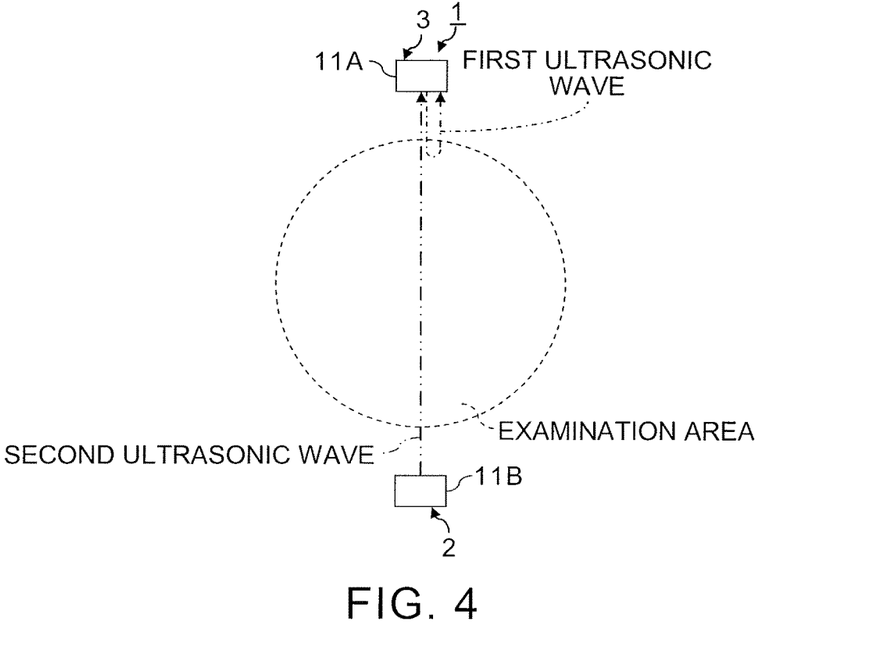
FIG. 4 shows the third example of fundamental structure of the ultrasonic transmission part and the ultrasonic detection part shown in FIG. 1.

FIG. 4 shows the third example of fundamental structure of the ultrasonic transmission part 2 and the ultrasonic detection part 3 shown in FIG. 1.

When the ultrasonic transducer 11 is used as a sensor of ultrasonic waves, the ultrasonic transmission part 2 and the ultrasonic detection part 3 can be composed using at least two ultrasonic transducers 11A, 11B as shown in FIG. 4.

Specifically, the first ultrasonic wave having a low frequency can be transmitted from the first ultrasonic transducer 11A toward a test region of a test target. Meanwhile, the second ultrasonic wave having a high frequency can be transmitted from a direction different from that of the first ultrasonic wave toward the test region of the test target by the second ultrasonic transducer 11B. Then, both of a reflected wave of the first ultrasonic wave reflected in the test region of the test target and the second ultrasonic wave which has passed through the test region can be received by the first ultrasonic transducer 11A.

That is, the first ultrasonic transducer 11A can have both a function as a sensor which receives ultrasonic waves and a function which transmits ultrasonic waves. In this case, the first ultrasonic transducer 11A is used as an element shared by both of the ultrasonic transmission part 2 and the ultrasonic detection part 3. Meanwhile, the second ultrasonic transducer 11B is used as an element of the ultrasonic transmission part 2.

The second ultrasonic transducer 11B is positioned so that the second ultrasonic wave which has passed through the test region of the test target can be detected by the first ultrasonic transducer 11A. For example, the first ultrasonic transducer 11A and the second ultrasonic transducer 11B can be disposed opposite to each other so that the test region of the test target lies between the first ultrasonic transducer 11A and the second ultrasonic transducer 11B.

Note that, the ultrasonic transmission part 2 and the ultrasonic detection part 3 may also be composed by combining the fundamental structures, shown in FIG. 2, FIG. 3, and FIG. 4, with each other. As a matter of course, the ultrasonic transmission part 2 and the ultrasonic detection part 3 can also be composed by disposing a plurality of fundamental structures in units of each fundamental structure shown in FIG. 2, FIG. 3, and FIG. 4.

Spherical waves without directivity may be used as the first ultrasonic wave having a low frequency and the second ultrasonic wave having a high frequency. Alternatively, when ultrasonic waves having directivity are used, detection of ultrasonic waves from unintended directions can be avoided. Therefore, using ultrasonic waves having directivity as the first ultrasonic wave and the second ultrasonic wave leads to improvement in SNR and accuracy. Note that, even when an ultrasonic wave having directivity is used, the ultrasonic wave actually spreads in the traveling direction of the ultrasonic wave. Therefore, the second ultrasonic wave can be detected as long as especially a sensor for detecting the second ultrasonic wave is disposed in a region where the second ultrasonic wave propagates, and it is not necessary to entirely oppose the sensor for detecting the second ultrasonic wave to the ultrasonic transducer 11 for transmitting the second ultrasonic wave.

From a viewpoint of improving SNR and accuracy, especially preferable ultrasonic waves include Lamb wave. Therefore, it is preferable to transmit Lamb waves as the first ultrasonic wave and the second ultrasonic wave. The Lamb wave propagates through a thin plate whose thickness is not more than half of a wavelength of ultrasonic wave, and include both a symmetric mode and an asymmetric mode.

When a sensor having reception directivity is used for detecting ultrasonic waves, detection of ultrasonic waves propagating from unnecessary directions can be avoided, and necessary ultrasonic signals can be selectively detected. Therefore, it is preferable to give directivity to both of a transmission element and a sensor of ultrasonic waves. Note that, in the case of giving directivity to both of a transmission element and a sensor of ultrasonic waves, it is necessary to dispose the transmission element and the sensor of ultrasonic waves so that a propagation area of an ultrasonic wave, which is a detection target, and an area in which an ultrasonic wave can be detected overlap with each other.

The optical fiber sensor 10, such as an FBG sensor, is a typical example of a sensor having reception directivity. Therefore, when the ultrasonic transmission part 2 and the ultrasonic detection part 3 are composed using the optical fiber sensor 10 as a sensor as shown in FIG. 2 and FIG. 3, detection accuracy of the first ultrasonic wave and the second ultrasonic wave can be improved. Meanwhile, when the ultrasonic transmission part 2 and the ultrasonic detection part 3 are composed using two ultrasonic transducers 11A and 11B as shown in FIG. 4, configuration of the ultrasonic transmission part 2 and the ultrasonic detection part 3 can be simplified.

The damage detection part 4 has a function to detect damage in a test region of a test target based on both of a reflected wave, of the first ultrasonic wave having a low frequency, reflected in the test region and the second ultrasonic wave, having a high frequency, which has passed through the test region. For that purpose, the damage detection part 4 also has a function to perform processing necessary for detecting an ultrasonic signal with a necessary SNR.

Examples of preprocessing for detecting a waveform of an ultrasonic signal include processing, such as averaging, noise removal processing, and envelope detection. In the case of performing averaging, an ultrasonic wave is transmitted and detected the required number of times. Then, ultrasonic signals detected over multiple times are added and averaged. The noise removal processing can be performed by filter processing using an LPF (low pass filter), an HPF (high pass filter) or the like for removing noise component from a detected ultrasonic signal, for example.

When the above-mentioned averaging and noise removal processing are performed as preprocessing, a sufficient SNR can be secured. Furthermore, when the envelope detection is performed, detection accuracy of a peak and analysis accuracy of a waveform can be improved.

Figure 5A:
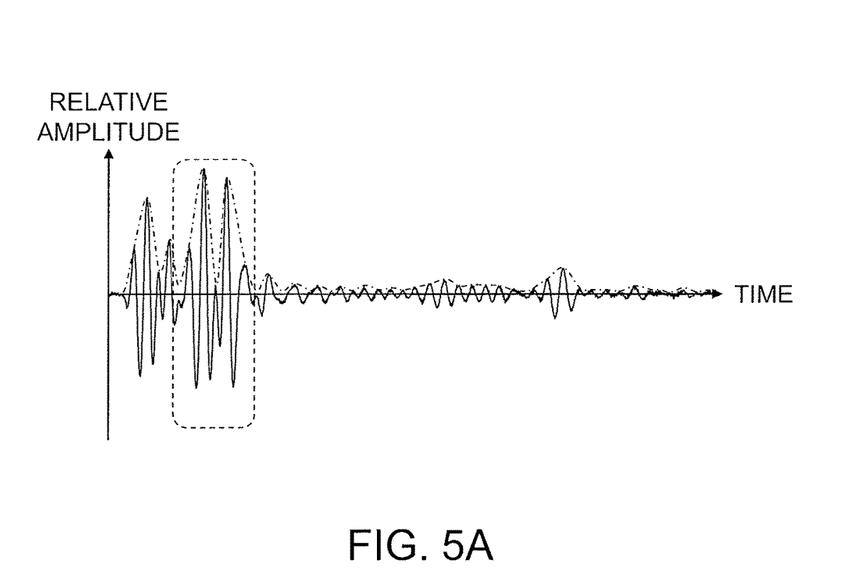
FIGS. 5A and 5B show an example of waveforms of reflected waves of the first ultrasonic waves each having a low frequency.
Figure 5B:
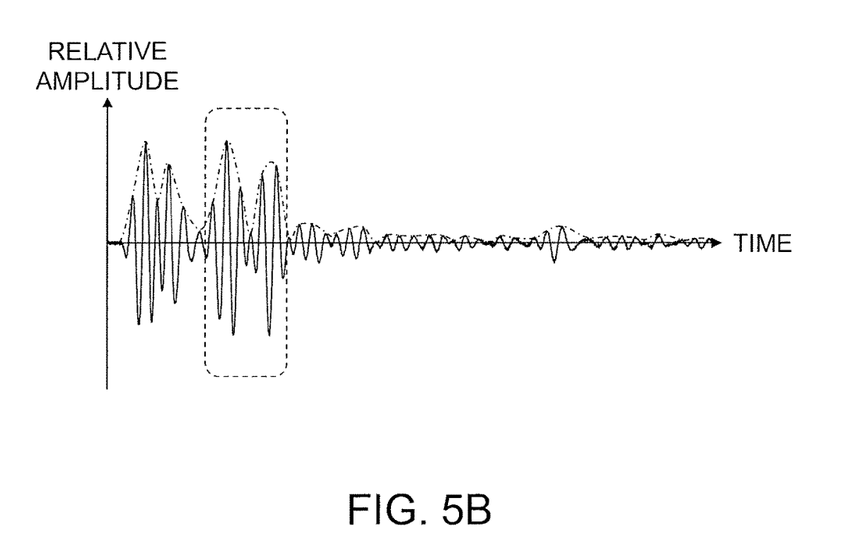

FIGS. 5A and 5B show an example of waveforms of reflected waves of the first ultrasonic waves each having a low frequency.

In FIGS. 5A and 5B, each vertical axis shows relative amplitude (relative intensity) of a detected signal by a sensor for detecting a reflected wave of the first ultrasonic wave while each horizontal axis shows elapsed time from transmission timing of the first ultrasonic wave. FIG. 5A shows a waveform of a detected signal, including a reflected wave of the first ultrasonic wave, detected by a sensor with targeting a test region without damage. Meanwhile, FIG. 5B shows a waveform of a detected signal, including a reflected wave of the first ultrasonic wave, detected by the sensor with targeting a test region in which damage exists. In FIGS. 5A and 5B, each solid line shows an averaged detected signal from the sensor while each dashed-dotted line shows an envelope curve of the detected signal obtained by envelope detection of the averaged detected signal.

As shown in FIGS. 5A and 5B, a peak position of reflected wave of the first ultrasonic wave changes depending on the existence of damage and a position of the damage in a test region. In the example shown in FIG. 5A, even when there is no damage, the reflected wave of the first ultrasonic wave reflected from an end portion of an adhesive object adhered to the test region or another structural object has been detected. Thus, a time corresponding to a peak of a waveform of reflected wave of the first ultrasonic wave reflected in a test region without damage can be previously obtained in order to identify the reflected wave of the first ultrasonic wave reflected at a damaged portion in the test region.

The reflected wave of the first ultrasonic wave reflected in the test region can be extracted from a detected signal by a sensor used for detecting the reflected wave of the first ultrasonic wave, based on a distance between the ultrasonic transducer 11 used for transmitting the first ultrasonic wave and the test region, a distance between the sensor and the test region, and the speed of sound in the test target.

Specifically, since a sum of a distance between the ultrasonic transducer 11 and the test region and a distance between the sensor and the test region is a propagation distance of the reflected wave of the first ultrasonic wave, a time range from transmission timing of the first ultrasonic wave by the ultrasonic transducer 11 to detection timing of the reflected wave of the first ultrasonic wave, reflected in the test region, by the sensor can be estimated based on the speed of sound. Then, a waveform portion in the calculated time range can be extracted from the detected signal as the reflected wave of the first ultrasonic wave reflected in the test region, as shown by each dotted line frame.

When the waveform of the reflected wave of the first ultrasonic wave reflected in the test region is extracted, a peak can be detected. It is practical to detect a peak from an envelope curve, in consideration of accuracy. When a peak is detected from the waveform of the reflected wave of the first ultrasonic wave, an elapsed time corresponding to the peak can be recorded as a reference time.

Then, based on a variation of a peak time of the reflected wave of the first ultrasonic wave, in the case that damage has occurred, from the reference time, whether damage has arisen and a position of the damage in the traveling direction of the first ultrasonic wave and the reflected wave can be detected. Specifically, an elapsed time corresponding to the peak of the reflected wave of the first ultrasonic wave in the case that damage has occurred can be obtained in a method similar to that for calculating the reference time. Next, a difference between the elapsed time corresponding to the peak of the reflected wave of the first ultrasonic wave and the reference time, i.e., a variation in the peak times of the reflected waves before and after the damage can be calculated.

Then, when the variation in the peak times of the reflected waves before and after the damage becomes not less than a threshold or when the variation becomes more than the threshold, it can be determined that damage exists. When it is determined that damage exists, a distance between the ultrasonic transducer 11 used for transmitting the first ultrasonic wave and the damaged portion, and a distance between a sensor used for detecting the reflected wave of the first ultrasonic wave and the damaged portion can be detected based on the peak time of the reflected wave of the first ultrasonic wave after the damage and the speed of sound. Thereby, a one-dimensional position of the damage in the traveling direction of the first ultrasonic wave and the reflected wave can be detected.

The difference between a reference peak time of the reflected wave of the first ultrasonic wave before the damage and the peak time of the reflected wave of the first ultrasonic wave after the damage has been generated due to peeling of an end portion of an adhesive object adhered to the test region. That is, it can be considered that the first ultrasonic wave reflected at the end portion of the adhesive object adhered to the test region before the damage. Meanwhile, it can be considered that the first ultrasonic wave reflected at a boundary between a region where the adhesive object had peeled and a region where the adhesive object had not peeled, without reflecting at the end portion of the adhesive object after the damage, as a result of the peeling of the end portion of the adhesive object. Therefore, a distance from the end portion of the adhesive object before peeling to the boundary between the region where the adhesive object has peeled and the region where the adhesive object has not peeled can be calculated based on the time difference between the reference peak time of the reflected wave of the first ultrasonic wave before the damage and the peak time of the reflected wave of the first ultrasonic wave after the damage.

As described above, the damage detection part 4 can detect a position of a damage, which exists in a test region, based on a period from transmission timing of the first ultrasonic wave having a low frequency, to timing when the reflected wave of the first ultrasonic wave shows a peak. Note that, when detection of the existence of damage and measurement of a distance of a peeled region from an end portion of an adhesive object are not performed based on the reflected wave of the first ultrasonic wave, acquisition of a reference time with targeting a test region without damage may be skipped.

Furthermore, when the first ultrasonic wave does not reflect in a test region before damage, such as a case where the damage is not peeling of an adhesive object but a crack in the test region, acquisition of a reference time with targeting the test region without the damage can also be skipped.

Figure 6A:
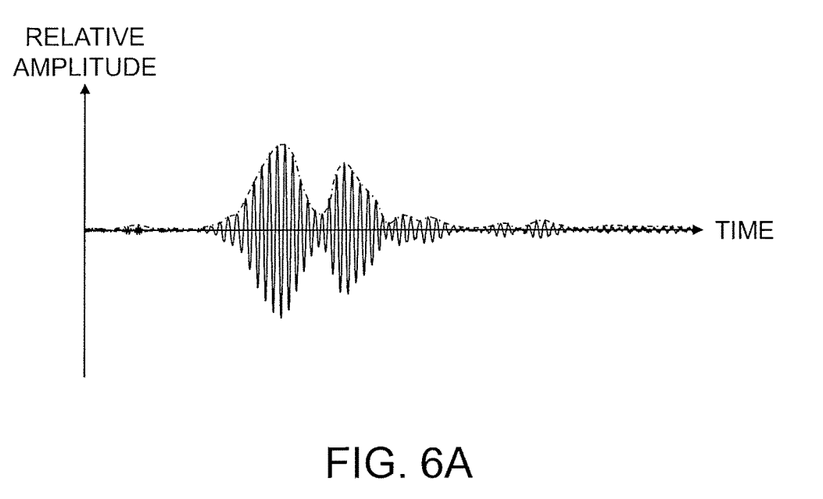
FIGS. 6A and 6B show an example of waveforms of the second ultrasonic waves each having a high frequency.
Figure 6B:
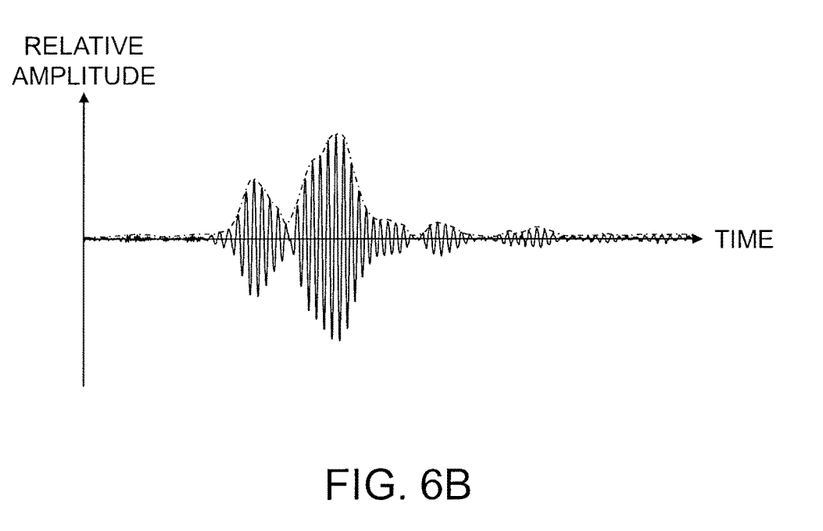

FIGS. 6A and 6B show an example of waveforms of the second ultrasonic waves each having a high frequency.

In FIGS. 6A and 6B, each vertical axis shows relative amplitude (relative intensity) of a detected signal by a sensor for detecting the second ultrasonic wave while each horizontal axis shows elapsed time from transmission timing of the second ultrasonic wave. FIG. 6A shows a waveform of a detected signal including the second ultrasonic wave, detected by the sensor with targeting a test region without damage. Meanwhile, FIG. 6B shows a waveform of a detected signal including the second ultrasonic wave, detected by the sensor with targeting a test region in which damage exists. In FIGS. 6A and 6B, each solid line shows an averaged detected signal by the sensor while each dashed-dotted line shows an envelope curve of the detected signal obtained by envelope detection of the averaged detected signal.

As shown in FIGS. 6A and 6B, the waveform of the second ultrasonic wave changes depending on the existence of damage in a test region. Thus, a waveform of the second ultrasonic wave can be previously obtained with targeting a test region without damage. A waveform of the second ultrasonic wave can be extracted from a detected signal by the sensor, based on the speed of sound and a propagation distance of ultrasonic wave, similarly to a waveform of reflected wave of the first ultrasonic wave. A waveform of the second ultrasonic wave corresponding to the test region without damage can be stored as a reference waveform.

Then, the existence of damage in a test region can be detected based on a change of a waveform of the second ultrasonic wave, in the case that the damage has occurred, from the reference waveform. A degree of the change of the waveform of the second ultrasonic wave, in the case that the damage has occurred, from the reference waveform can be expressed using an index, such as a cross-correlation coefficient or a square error. It is practical to also compare waveforms of envelope curves with each other, in consideration of accuracy.

When an index showing a variation of the waveform of the second ultrasonic wave, in the case that damage has occurred, from the reference waveform is obtained, the existence of the damage can be determined by threshold processing of the index. Specifically, when the variation of the waveform becomes not less than a threshold or when the variation becomes more than the threshold, it can be determined that a damage exists in the test region.

As described above, the damage detection part 4 can detect the existence of damage in a test region based on a variation of the waveform of the second ultrasonic wave having a high frequency.

The damage detection part 4 may also be configured to be able to measure a length of delamination or peeling, in addition to detecting the existence of damage and detecting a position of the damage in a test region. As a method of measuring a damage length, the method described in Japanese Patent Application Publication JP 2011-185921 A can be used, for example.

The damage detection part 4 having the functions as described above can be composed of a computer reading program. At least one circuit may also be used to compose the damage detection part 4. A computer is also composed of electronic circuitry. Therefore, when a computer is assumed to be a kind of circuitry, it can also be said that the damage detection part 4 can be composed of circuitry.

(Operation and Action)

Next, an ultrasonic test method of a test target using the ultrasonic test system 1 will be described.

Figure 7:
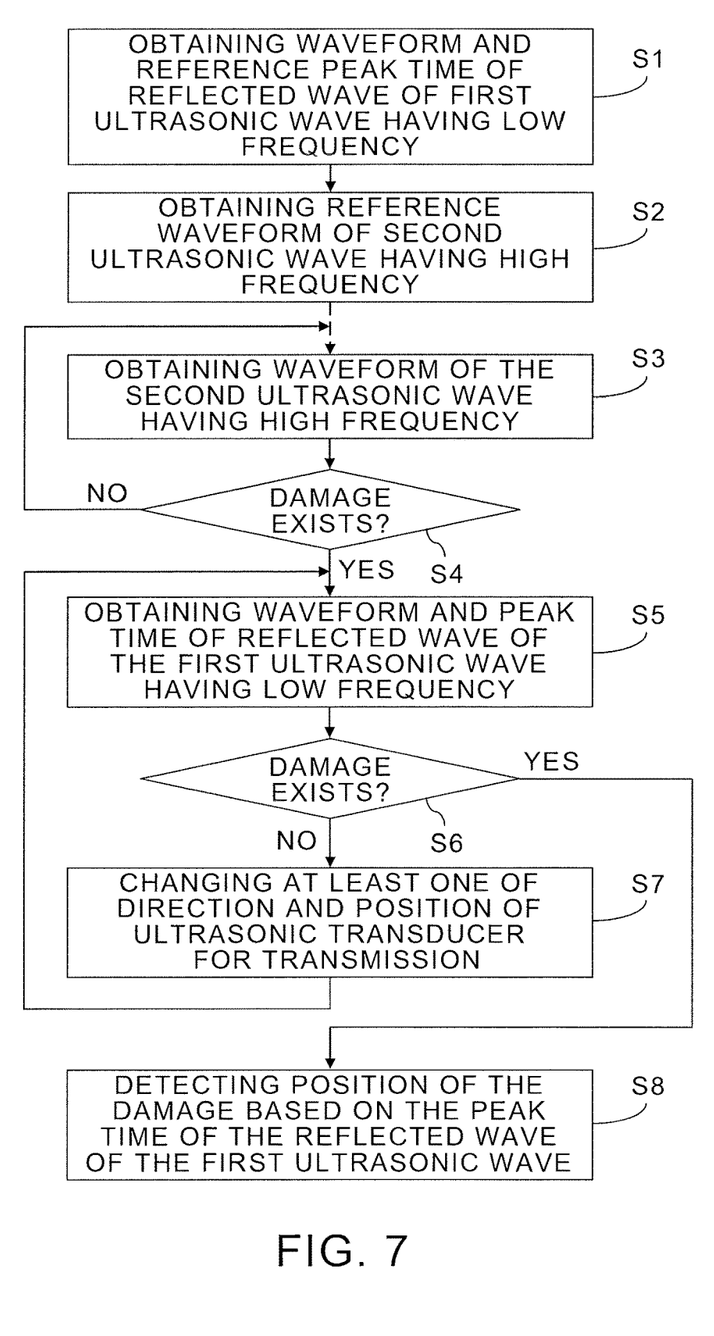
FIG. 7 is a flow chart showing an example flow in a case of performing a flaw detection test in a test region of a test target by the ultrasonic test system shown in FIG. 1.

FIG. 7 is a flow chart showing an example flow in a case of performing a flaw detection test in a test region of a test target by the ultrasonic test system 1 shown in FIG. 1.

Firstly, in step S1, the first ultrasonic wave having a low frequency is transmitted from the ultrasonic transducer 11 of the ultrasonic transmission part 2 toward a test region of a test target without damage. Then, the reflected wave of the first ultrasonic wave reflected in the test region is detected by a sensor of the ultrasonic detection part 3. The detected signal including the detected reflected wave of the first ultrasonic wave is output to the damage detection part 4. The damage detection part 4 detects a peak time of the reflected wave of the first ultrasonic wave. The detected peak time of the reflected wave of the first ultrasonic wave is recorded in the damage detection part 4 as a reference peak time.

Next, in step S2, the second ultrasonic wave having a high frequency is transmitted from the ultrasonic transducer 11 of the ultrasonic transmission part 2 toward the test region of the test target without damage. Then, the second ultrasonic wave which has passed through the test region is detected by a sensor of the ultrasonic detection part 3. The detected signal including the detected second ultrasonic wave is output to the damage detection part 4. The damage detection part 4 detects the waveform of the second ultrasonic wave. The detected waveform of the second ultrasonic wave is recorded in the damage detection part 4 as a reference waveform.

Note that, the order of step S1 and step S2 is arbitrary. Furthermore, when the reference peak time of the reflected wave of the first ultrasonic wave is not used for detecting a damage, step S1 may be skipped. Then, when at least the reference waveform of the second ultrasonic wave corresponding to the test region of the test target without damage is obtained, to monitor whether a damage has occurred in the test region becomes possible. Alternatively, it becomes possible to sequentially inspect the existence of damage with targeting test regions of a large number of test targets each having a similar form.

In the case of inspecting the same or another test target, the second ultrasonic wave having a high frequency is transmitted from the ultrasonic transducer 11 of the ultrasonic transmission part 2 toward the test region of the test target, in step S3. Then, the second ultrasonic wave which has passed through the test region of the test target is detected by the sensor of the ultrasonic detection part 3. The detected signal including the detected second ultrasonic wave is output to the damage detection part 4. The damage detection part 4 detects the waveform of the second ultrasonic wave.

Next, in step S4, the damage detection part 4 determines whether a damage exists in the test region to which the second ultrasonic wave has been transmitted, by comparing the waveform of the second ultrasonic wave with the reference waveform. Specifically, whether a damage exists in the test region to which the second ultrasonic wave has been transmitted is determined by threshold processing of an index showing a difference between the waveform of the second ultrasonic wave and the reference waveform.

Then, when a damage has been determined not to exist, transmission of the second ultrasonic wave having a high frequency can be intermittently repeated until a damage is determined to exist. Alternatively, when flaw detection tests of plural test targets like aircraft parts sequentially manufactured in a production line are performed, an inspection can be started by transmitting the second ultrasonic wave having a high frequency to another test target.

Meanwhile, when a damage has been determined to exist, the first ultrasonic wave having a low frequency is transmitted from the ultrasonic transducer 11 of the ultrasonic transmission part 2 toward the test region of the test target, in step S5. Then, the reflected wave of the first ultrasonic wave, reflected in the test region of the test target, is detected by the sensor of the ultrasonic detection part 3. The detected signal including the detected reflected wave of the first ultrasonic wave is output to the damage detection part 4. The damage detection part 4 detects the waveform and the peak time of the reflected wave of the first ultrasonic wave.

Next, in step S6, the damage detection part 4 determines whether a damage exists in the test region to which the first ultrasonic wave has been transmitted, by comparing the peak time of the reflected wave of the first ultrasonic wave with the reference peak time. Specifically, whether a damage exists in the test region to which the first ultrasonic wave has been transmitted is determined by threshold processing of a difference between the peak time of the reflected wave of the first ultrasonic wave and the reference peak time.

When a damage has been determined not to exist, it means that the first ultrasonic wave has not reflected on the damage confirmed in the test region by transmitting the second ultrasonic wave. Therefore, at least one of a direction and a position of the ultrasonic transducer 11 for transmission is changed in step S7. Then, a waveform and a peak time of reflected wave of the first ultrasonic wave are obtained again. Note that, at least one of a direction and a position of the ultrasonic transducer 11 for transmission may be changed before the first transmission of the first ultrasonic wave.

Meanwhile, when a damage has been determined to exist, the damage detection part 4 detects a position of the damage based on the peak time of the reflected wave of the first ultrasonic wave, in step S8. Furthermore, when the damage is peeling of an adhesive object, a length of a region where the adhesive object has been peeled off can also be detected based on a time difference between the reference peak time and the peak time. Thereby, the existence of damage in the test region of the test target and a position of the detected damage can be confirmed.

Next, an example method of manufacturing an aircraft part with a monitoring of damage using the ultrasonic test system 1 will be described.

Figure 8:
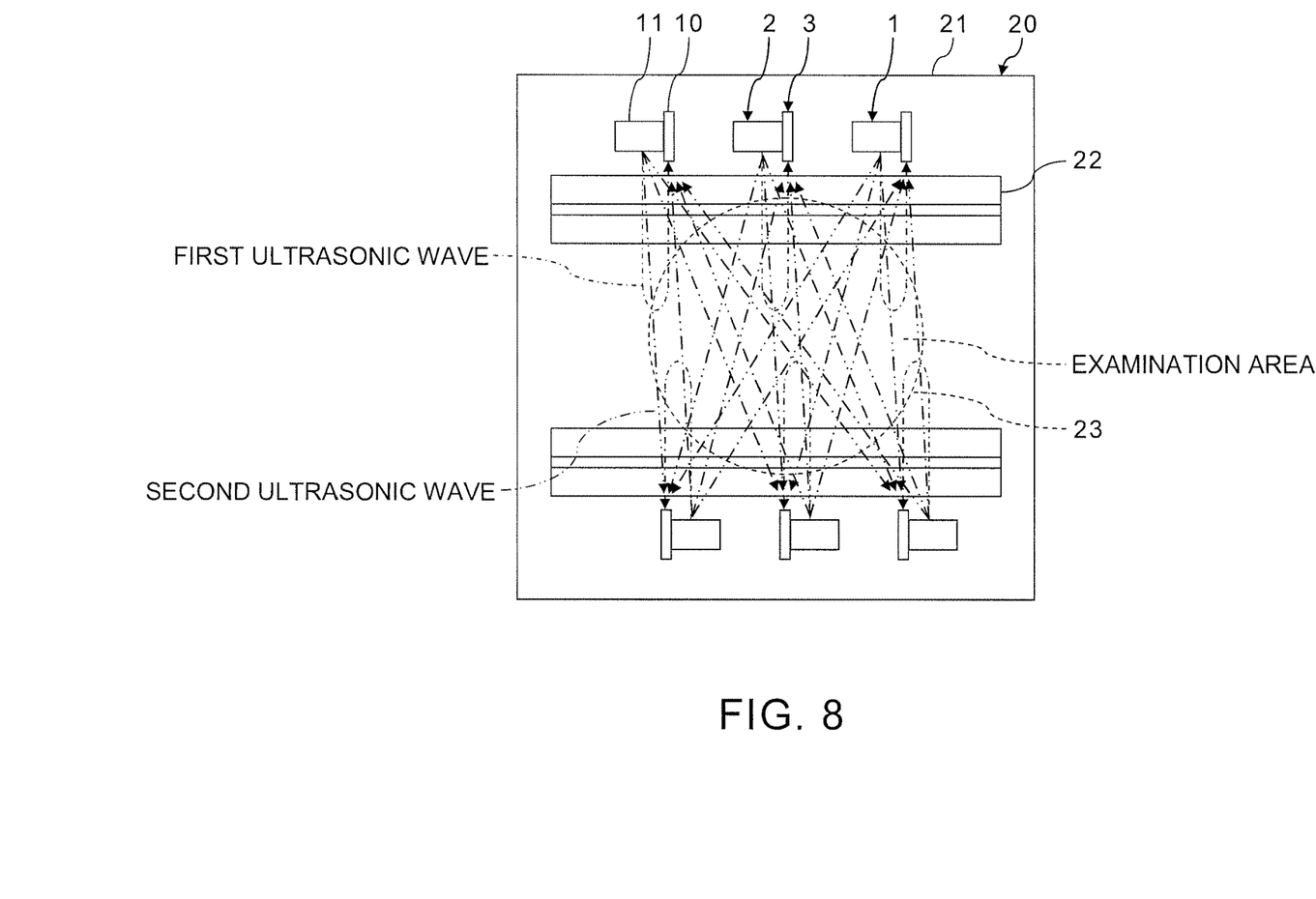
FIG. 8 shows an example of disposing the ultrasonic transducers and the optical fiber sensors on an aircraft part which is a monitoring target of damage by the ultrasonic test system shown in FIG. 1.
Figure 9:
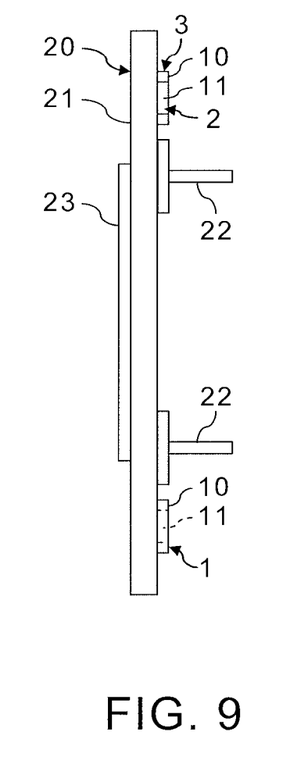
FIG. 9 is a left side view of the aircraft part shown in FIG. 8.

FIG. 8 shows an example of disposing the ultrasonic transducers 11 and the optical fiber sensors 10 on an aircraft part which is a monitoring target of damage by the ultrasonic test system 1 shown in FIG. 1. FIG. 9 is a left side view of the aircraft part shown in FIG. 8.

When a minor damage has occurred on a surface of an aircraft part 20 which is mainly made of a composite material, such as CFRP (carbon fiber reinforced plastics), a disk-shaped patch 23 is sometimes bonded to a region including a part to be repaired of the aircraft part 20, in order to repair the damage. In the example shown in FIG. 8, the aircraft part 20 including a panel 21 of which stringers 22 have been disposed on one side is a target to be repaired. The patch 23 has been bonded on the other side of the panel 21, on which the stringers 22 have not been disposed.

In such a case, the existence of peeling of the patch 23 can be monitored using the ultrasonic test system 1. Specifically, the plural ultrasonic transducers 11 and the plural optical fiber sensors 10 can be disposed around the patch 23 so that peeling of the patch 23 can be detected. In the example shown in FIG. 8, six sets of the ultrasonic transducers 11 and the optical fiber sensors 10 have been disposed at positions surrounding the patch 23 within a range where the second ultrasonic waves can be transmitted and received mutually.

In the example shown in FIG. 8, the ultrasonic transducers 11 and the optical fiber sensors 10 have been attached to the surface of the panel 21, on which the patch 23 has not been bonded, that is, the surface of the panel 21 opposite to the patch 23 side. Alternatively, the ultrasonic transducers 11 and the optical fiber sensors 10 may be attached to the surface of the panel 21, on which the patch 23 has been bonded, that is, the surface in the patch 23 side of the panel 21. Furthermore, the ultrasonic transducers 11 and the optical fiber sensors 10 may also be attached on the patch 23.

It is important to attach the ultrasonic transducers 11 and the optical fiber sensors 10 on a same side of the panel 21 in order to detect the existence of peeling of the patch 23 in a satisfactory accuracy. In particular, to attach the ultrasonic transducers 11 and the optical fiber sensors 10 on the patch 23 side of the panel 21 leads to improvement in the detection accuracy of the existence of peeling of the patch 23. Nevertheless, it may be difficult to attach the ultrasonic transducers 11 and the optical fiber sensors 10 on the patch 23 side of the panel 21 because of a structure of the aircraft part 20. In such a case, even when the ultrasonic transducers 11 and the optical fiber sensors 10 are attached on the surface of the panel 21 opposite to the patch 23 side as shown in FIG. 8, the existence of peeling of the patch 23 can be detected in a sufficient accuracy.

More specifically, the first ultrasonic wave having a low frequency and the second ultrasonic wave having a high frequency can be transmitted to a test region which is a boundary surface between a region including a part to be repaired and the patch 23. Then, a reflected wave of the first ultrasonic wave in the test region and the second ultrasonic wave which has passed through the test region can be obtained as information for monitoring whether a damage has occurred in the test region.

Therefore, the part to be repaired of the aircraft part 20 can be repaired with confirming that a damage, such as peeling, of the patch 23 has not occurred. Thereby, the repaired aircraft part 20 can be manufactured.

As a result of actually detecting peeling of the patch 23, which has been artificially progressed, using the ultrasonic test system 1, it was confirmed that a form of a peeling region of the patch 23 can be mostly detected. In this test, six sets of the ultrasonic transducers 11 and the optical fiber sensors 10 were used as shown in FIG. 8, and the first ultrasonic waves each having a frequency approximately from 50 kHz to 100 kHz were transmitted and received mutually. Similarly, the second ultrasonic waves each having a frequency of approximately 400 kHz were also transmitted and received mutually using the six sets of the ultrasonic transducers 11 and the optical fiber sensors 10.

Then, the entire waveforms of the second ultrasonic waves before and after the occurrence of damage were subjected to a frequency analysis in the time domain, and the existence of a waveform change in the second ultrasonic wave was determined based on self correlativity. Furthermore, a position at an end portion of a peeling region of the patch 23 was obtained, as a position where the first ultrasonic wave was reflected, based on a change in time, before and after the damage, at which a reflected wave of the first ultrasonic wave reached each of the optical fiber sensors 10, and a speed of ultrasonic wave. As a result, it was confirmed that the position at the end portion of the peeling region of the patch 23, which changes due to repetition of progress of the damage, can be detected in a satisfactory accuracy.

That is, the ultrasonic test system 1 and the ultrasonic test method as described above are to detect a damage, such as delamination or a crack, in an adhesive part or a joined part using two kinds of ultrasonic waves whose center frequencies are different from each other. Specifically, the ultrasonic test system 1 and the ultrasonic test method allow inspecting the existence of a damage, with targeting a large test region using the second ultrasonic wave whose frequency band is high, and detecting a position of the damage using a reflected wave of the first ultrasonic wave whose frequency band is low.

(Effects)

Therefore, the ultrasonic test system 1 and the ultrasonic test method allow detecting a damage with high accuracy, with targeting a test region larger than that of the conventional method.

Conventionally, a method of detecting a damage by detecting a reflected wave reflected in a damaged part has been performed using only an ultrasonic wave having a low frequency approximately from 50 kHz to 100 kHz. However, using an ultrasonic wave having a low frequency can detect only a damage which exists in the traveling direction of the ultrasonic wave and exists in a short distance. That is, when only an ultrasonic wave having a low frequency is used, detection of a damage over a wide range becomes difficult.

By contrast, the ultrasonic test system 1 and the ultrasonic test method allow detecting a damage over a wider range than that in the conventional method since a transmitted wave of the second ultrasonic wave having a high frequency is used in addition to a reflected wave of the first ultrasonic wave having a low frequency. As a result, when a flaw detection inspection is performed with targeting a large test region, not only damage detection accuracy can be improved, but also the number of sensors can be reduced.

While certain implementations have been described, these implementations have been presented by way of example only, and are not intended to limit the scope of the invention. Indeed, the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms or modifications as would fall within the scope and spirit of the invention.

What is claimed is:

1. An ultrasonic test system comprising:
   at least one ultrasonic transducer that transmits a first ultrasonic wave and a second ultrasonic wave toward a test region, the first ultrasonic wave having a relatively low frequency, the second ultrasonic wave having a frequency higher than the frequency of the first ultrasonic wave;
   at least one sensor that detects a reflected wave of the first ultrasonic wave and the second ultrasonic wave which has passed through the test region, the reflected wave being from the test region; and
   damage detection circuitry configured to detect a damage in the test region, based on the reflected wave of the first ultrasonic wave and the second ultrasonic wave which has passed through the test region, wherein the at least one sensor comprises:
   a first optical fiber sensor that detects the reflected wave of the first ultrasonic wave; and
   a second optical fiber sensor that detects the ultrasonic wave which has passed through the test region.

2. An ultrasonic test system comprising:
   at least one ultrasonic transducer that transmits a first ultrasonic wave and a second ultrasonic wave toward a test region, the first ultrasonic wave having a relatively low frequency, the second ultrasonic wave having a frequency higher than the frequency of the first ultrasonic wave;
   at least one sensor that detects a reflected wave of the first ultrasonic wave and the second ultrasonic wave which has passed through the test region, the reflected wave being from the test region; and
   damage detection circuitry configured to detect a damage in the test region, based on the reflected wave of the first ultrasonic wave and the second ultrasonic wave which has passed through the test region;
   and where the at least one ultrasonic transducer comprises:
   a first ultrasonic transducer that transmits the first ultrasonic wave toward the test region; and
   a second ultrasonic transducer that transmits the second ultrasonic wave toward the test region from a direction different from a direction of the first ultrasonic wave; and wherein the at least one sensor comprises:
   at least one optical fiber sensor that detects the reflected wave of the first ultrasonic wave and the second ultrasonic wave which has passed through the test region.

3. The ultrasonic test system according to claim 1, wherein the at least one ultrasonic transducer comprises:
   a first ultrasonic transducer that transmits the first ultrasonic wave toward the test region; and
   a second ultrasonic transducer that transmits the second ultrasonic wave toward the test region from a direction different from a direction of the first ultrasonic wave, and
   wherein the first ultrasonic transducer is configured to receive the reflected wave of the first ultrasonic wave and the second ultrasonic wave which has passed through the test region.

4. The ultrasonic test system according to claim 1, wherein the at least one ultrasonic transducer is configured to transmit an ultrasonic wave, of which frequency is not less than 75 kHz and not more than 125 kHz, as the first ultrasonic wave.

5. The ultrasonic test system according to claim 1, wherein the at least one ultrasonic transducer is configured to transmit an ultrasonic wave, of which frequency is not less than 300 kHz and not more than 400 kHz, as the second ultrasonic wave.

6. The ultrasonic test system according to claim 1, wherein the at least one ultrasonic transducer is configured to transmit Lamb waves as the first ultrasonic wave and the second ultrasonic wave respectively.

7. The ultrasonic test system according to claim 1, wherein the damage detection circuitry is configured to:
   detect an existence of the damage based on a variation of a waveform of the second ultrasonic wave; and
   detect a position of the damage based on a period from transmission timing of the first ultrasonic wave to timing when the reflected wave of the first ultrasonic wave shows a peak.

8. An ultrasonic test method comprising: operating the ultrasonic test system of claim 1 by;
   transmitting the first ultrasonic wave and the second ultrasonic wave, from the at least one ultrasonic transducer that transmits the first ultrasonic wave and the second ultrasonic wave, toward a test region, the first ultrasonic wave having a relatively low frequency, the second ultrasonic wave having a frequency higher than the frequency of the first ultrasonic wave;
   detecting the reflected wave of the first ultrasonic wave and the second ultrasonic wave which has passed through the test region, the reflected wave being from the test region; and
   detecting a damage in the test region, based on the reflected wave of the first ultrasonic wave and the second ultrasonic wave which has passed through the test region.

9. A method of manufacturing an aircraft part comprising:
   bonding a patch to a region including a part to be repaired of an aircraft part;

transmitting, with the ultrasonic test system of claim 1, a first ultrasonic wave and a second ultrasonic wave toward a test region, the first ultrasonic wave having a relatively low frequency, the second ultrasonic wave having a frequency higher than the frequency of the first ultrasonic wave, the test region being a boundary surface between the region including the part to be repaired and the patch;

obtaining a reflected wave of the first ultrasonic wave and the second ultrasonic wave which has passed through the test region, the reflected wave being from the test region, the reflected wave and the second ultrasonic wave serving as information for monitoring whether a damage has occurred in the test region; and manufacturing a repaired aircraft part by repairing the part to be repaired of the aircraft part.

10. The ultrasonic test system according to claim 2, wherein the at least one ultrasonic transducer is configured to transmit an ultrasonic wave, of which frequency is not less than 75 kHz and not more than 125 kHz, as the first ultrasonic wave.

11. The ultrasonic test system according to claim 3, wherein the at least one ultrasonic transducer is configured to transmit an ultrasonic wave, of which frequency is not less than 75 kHz and not more than 125 kHz, as the first ultrasonic wave.

12. The ultrasonic test system according to claim 10, wherein the at least one ultrasonic transducer is configured to transmit an ultrasonic wave, of which frequency is not less than 300 kHz and not more than 400 kHz, as the second ultrasonic wave.

13. The ultrasonic test system according to claim 2, wherein the at least one ultrasonic transducer is configured to transmit an ultrasonic wave, of which frequency is not less than 300 kHz and not more than 400 kHz, as the second ultrasonic wave.

14. The ultrasonic test system according to claim 3, wherein the at least one ultrasonic transducer is configured to transmit an ultrasonic wave, of which frequency is not less than 300 kHz and not more than 400 kHz, as the second ultrasonic wave.

15. The ultrasonic test system according to claim 4, wherein the at least one ultrasonic transducer is configured to transmit an ultrasonic wave, of which frequency is not less than 300 kHz and not more than 400 kHz, as the second ultrasonic wave.

16. The ultrasonic test system according to claim 2, wherein the at least one ultrasonic transducer is configured to transmit Lamb waves as the first ultrasonic wave and the second ultrasonic wave respectively.

17. The ultrasonic test system according to claim 3, wherein the at least one ultrasonic transducer is configured to transmit Lamb waves as the first ultrasonic wave and the second ultrasonic wave respectively.

18. An ultrasonic test system comprising:

an ultrasonic transducer that transmits a first ultrasonic wave and a second ultrasonic wave toward a test region, the first ultrasonic wave having a relatively low frequency, the second ultrasonic wave having a frequency higher than the frequency of the first ultrasonic wave;

at least one sensor that detects a reflected wave of the first ultrasonic wave and the second ultrasonic wave which has passed through the test region, the reflected wave being from the test region; and damage detection circuitry configured to detect a damage in the test region, based on the reflected wave of the first ultrasonic wave and the second ultrasonic wave which has passed through the test region, and wherein the at least one sensor comprises a first sensor and a second sensor, and wherein the first ultrasonic wave and the second ultrasonic wave sent by the ultrasonic transducer is sensed, respectively, by the first sensor and the second sensor.

19. An ultrasonic test system comprising:

at least one ultrasonic transducer that transmits a first ultrasonic wave and a second ultrasonic wave toward a test region, the first ultrasonic wave having a relatively low frequency, the second ultrasonic wave having a frequency higher than the frequency of the first ultrasonic wave;

at least one sensor that detects a reflected wave of the first ultrasonic wave and the second ultrasonic wave which has passed through the test region, the reflected wave being from the test region; and damage detection circuitry configured to detect a damage in the test region, based on the reflected wave of the first ultrasonic wave and the second ultrasonic wave which has passed through the test region, and wherein one of the at least one ultrasonic transducer transmits the first ultrasonic wave and the second ultrasonic wave to respective first and second sensors.

20. The ultrasonic test system of claim 1, wherein the at least one ultrasonic transducer includes a first ultrasonic transducer, and each of the first ultrasonic transducer and to first optical sensor are positioned on a common side of the test region.

21. An ultrasonic test method comprising operating the ultrasonic test system of claim 2 by:

transmitting the first ultrasonic wave and the second ultrasonic wave, from the at least one ultrasonic transducer that transmits the first ultrasonic wave and the second ultrasonic wave, toward a test region, the first ultrasonic wave having a relatively low frequency, the second ultrasonic wave having a frequency higher than the frequency of the first ultrasonic wave;

detecting the reflected wave of the first ultrasonic wave and the second ultrasonic wave which has passed through the test region, the reflected wave being from the test region; and detecting a damage in the test region, based on the reflected wave of the first ultrasonic wave and the second ultrasonic wave which has passed through the test region.

22. A method of manufacturing an aircraft part comprising:

bonding a patch to a region including a part to be repaired of an aircraft part;

transmitting, with the ultrasonic test system of claim 2, a first ultrasonic wave and a second ultrasonic wave toward a test region, the first ultrasonic wave having a relatively low frequency, the second ultrasonic wave having a frequency higher than the frequency of the first ultrasonic wave, the test region being a boundary surface between the region including the part to be repaired and the patch;

obtaining a reflected wave of the first ultrasonic wave and the second ultrasonic wave which has passed through the test region, the reflected wave being from the test region, the reflected wave and the second ultrasonic wave serving as information for monitoring whether a damage has occurred in the test region; and manufacturing a repaired aircraft part by repairing the part to be repaired of the aircraft part.

\* \* \* \* \*